United States Patent [19]
Horrobin et al.

[11] Patent Number: 6,069,168
[45] Date of Patent: May 30, 2000

[54] COMPOSITIONS FOR TREATMENT OF DIABETIC COMPLICATIONS

[75] Inventors: David Frederick Horrobin; Mary Cotter; Norman Cameron, all of Guildford, United Kingdom

[73] Assignee: Scotia Holdings Plc, United Kingdom

[21] Appl. No.: 08/796,901

[22] Filed: Feb. 6, 1997

Related U.S. Application Data

[63] Continuation of application No. 08/491,244, Jun. 16, 1995, abandoned.

[30] Foreign Application Priority Data

Jun. 28, 1994 [GB] United Kingdom .................. 9412925
Nov. 4, 1994 [GB] United Kingdom .................. 9422338

[51] Int. Cl.$^7$ .......................... A61K 31/34; A61K 31/20
[52] U.S. Cl. ........................................... 514/474; 514/560
[58] Field of Search ..................... 514/560, 474

[56] References Cited

U.S. PATENT DOCUMENTS

| | | | |
|---|---|---|---|
| 4,388,324 | 6/1983 | Horrobin ................................ | 514/474 |
| 4,826,877 | 5/1989 | Stewart et al. ......................... | 514/560 |
| 5,009,891 | 4/1991 | Niwa et al. ........................... | 424/195.1 |
| 5,078,989 | 1/1992 | Ando et al. . | |
| 5,114,716 | 5/1992 | N'Guyen et al. ....................... | 424/401 |
| 5,278,189 | 1/1994 | Rath et al. ............................. | 514/561 |

FOREIGN PATENT DOCUMENTS

| | | |
|---|---|---|
| 0 019 423 | 4/1981 | European Pat. Off. . |
| 0 115 419 | 1/1985 | European Pat. Off. . |
| 0 175 468 | 7/1985 | European Pat. Off. . |
| 0 139 480 | 8/1985 | European Pat. Off. . |
| 0 195 570 | 1/1987 | European Pat. Off. . |
| 0 201 159 | 3/1987 | European Pat. Off. . |
| 0 266 323 | 8/1988 | European Pat. Off. . |
| 0 283 140 | 3/1989 | European Pat. Off. . |
| 0 309 086 | 8/1989 | European Pat. Off. . |
| 0 222 483 | 9/1989 | European Pat. Off. . |
| 0 334 507 | 2/1990 | European Pat. Off. . |
| 0 347 056 | 3/1990 | European Pat. Off. . |
| 0 364 094 | 7/1990 | European Pat. Off. . |
| 0 416 855 | 2/1991 | European Pat. Off. . |
| 0 409 559 | 3/1991 | European Pat. Off. . |
| 0 440 308 | 11/1991 | European Pat. Off. . |

OTHER PUBLICATIONS

Horrobin, Agents Actions (Switzerland), 37/suppl., pp. 120–144, 1992.
Stracke et al.,, Innere Medizin, 48, pp.259–261, 1993.
Gen Pharmacol, vol. 21, No. 1, pp. 135–140, 1990; Law et al: "Effects of Ponalrestat on Depressor Responses to Arachidonic Acid in Streptozoticon–diabetic Rats," (p. 138, col. 2, line 10–line 29).
Nervenheilkunde (Germany), 1993, vol. 12, No. 7, pp. 405–410; Ziegler et al: "Diabetische Neuropathie: Pathogenetische Konzepte Und Potentielle Therapeutische Konsequenzen"; p. 406, col. 2, line 39–60; page 407, col. 3, line 8–22.
Dtsch. Med. Wochenschr. (Germany, Federal Republic of), 1991, vol. 116, No. 18, pp. 716–717; Ziegler et al: "Pain treatment in diabetic polyneuropathy"; p. 716, col. 2, line 25–49.
Diabetic Med. (United Kingdom), 1993, vol. 10, Suppl. 2, pp. 4S–6S; Ward: "Progress and Treatment in Diabetic Neuropathy"; p. 55, col. 2, line 13–15.
Patent Abstracts of Japan, C field, vol. 11, No. 282 Sep. 1987 p 103 C 446 JP 62–81 307 Kanebo.
Chem. Abs. vol. 107, 1987 83706m p. 33707 Kanebo.
Patent Abstract of Japan 06093284 A Apr. 94 Hiroshi et al Highly Stable Perilla Oil and Cosmetic Base Material Contianing the Perilla Oil as Active Ingredient.
Garrison et al. "The Nutrition Desk Reference", published by Keating Publishing, Inc., pp. 95 and 96, 1985.
Embase abstract of Horrobin, "The use of gamma–linolenic acid in diabetic neuropathy", Agents Actions (Switzerland), 37/suppl. (120144) 1992.
Embase abstract of Stracke et al., "Diagnosis and therapy of diabetic polyneurpathy" Z Gesamte Inn Med (Germany), 48(5) pp. 259–261, 1993.
Martindale 28th Edition, p. 1653 (Jul. 23, 1985).
USP 21st Edition, pp. 75–76 (Jun. 24 1986).
The Merck Index, 10th Edition, p. 120 (1993.

*Primary Examiner*—Raymond Henley, III
*Attorney, Agent, or Firm*—Nixon & Vanderhye

[57] ABSTRACT

Use of 6-desaturated n-6 fatty acids, especially gammalinolenic acid (GLA), dihomogammalinolenic acid (DGLA) or arachidonic acid (AA), together with a pharmaceutically acceptable material reducing intracellular levels of sorbitol in the body, particularly an aldose reductase inhibitor, in the treatment of (including prophylactic treatment), and in the preparation of medicaments for the treatment of (including prophylactic treatment), the long-term complications of diabetes mellitus. Pharmaceutical compositions of said materials. The ascorbate esters of 6-desaturated n-6 fatty acids (other than GLA or DGLA) per se.

11 Claims, 3 Drawing Sheets

NC = normal control: D = diabetic untreated: DE= diabetic treated with GLA at 8 mg/kg/day: DZ = diabetic treated with ZD5522 at 0.25mg/kg/day: DW = diabetic treated with WAY121509 at 0.2mg/kg/day: DEZ = diabetic treated with GLA + ZD5522 at the same doses: DEW = diabetic treated with GLA + WAY121509 at the same doses.

C = normal control: D = diabetic untreated: DVA = diabetic treated with 20mg/kg/day ascorbic acid: DG treated with 8mg/kg/day GLA: DG + C: diabetic treated with GLA and ascorbic acid at the same doses: DASG: diabetic treated with ascorbyl-GLA to provide approximately the equivlent of 8mg/kg/day GLA

COMPOSITIONS FOR TREATMENT OF DIABETIC COMPLICATIONS

This is a Rule 62 File Wrapper Continuation of application Ser. No. 08/491,244, filed Jun. 16, 1995, now abandoned.

BACKGROUND

Diabetes mellitus is a common disease which is usually classified into insulin-dependent and non-insulin dependent types. Both types may be managed by diet, in association with insulin in the first type and a variety of drugs in the second. However, while the changes in blood glucose can usually be managed reasonably satisfactorily by conscientious patients and doctors, this does not prevent long term damage to many tissues as a result of the disease. This damage may take many forms but the major types are damage to the eyes, (retinopathy), nerves (neuropathy), kidneys (nephropathy) and cardiovascular system. While some patients develop isolated damage to one system or another, in most patients two or more types of damage occur together suggesting that the underlying mechanism is similar.

There are many approaches to reducing or preventing these forms of damage, which are collectively known as the long term complications of diabetes. This patent specification concerns two of them.

One approach is based on essential fatty acid (EFA) metabolism being deranged with a block in the conversion of the main dietary EFA, linoleic acid, to its first metabolite, gamma-linolenic acid (GLA) the first of the '6-desaturated' n-6 EFAs in the sequence shown in Table I below (in this context it should be noted that the term '6-desaturated EFAs' means EFAs beyond the 6-desaturation step and does not necessarily mean that the EFA has a double bond in the 6-position):

TABLE 1

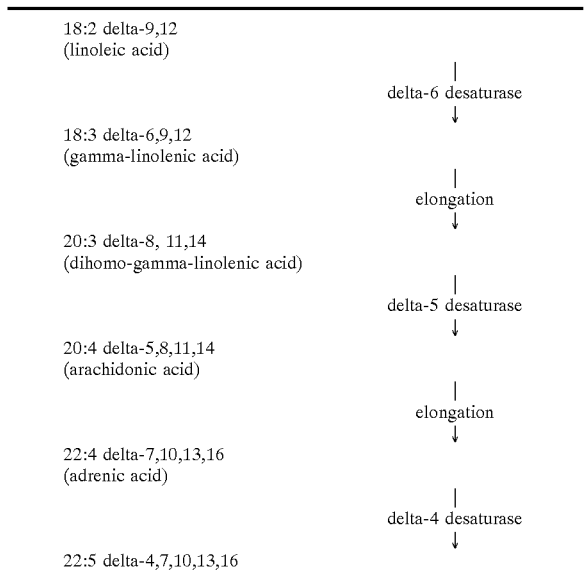

As a consequence the levels of metabolites of GLA, including dihomogamma linolenic acid (DGLA) and arachidonic acid (AA), are reduced. Since these metabolites are important components of the structure of the membranes of nerves and of cells in all tissues, and since they are the precursors and constituents of cellular signalling systems such as prostaglandins and diacylglycerols, deficits of these compounds are damaging. In particular there is a deficit of prostaglandin $E_1$ derived from DGLA and of prostacyclin derived from arachidonic acid, both of which are vasodilating agents essential for maintaining blood flow to the microcirculation in many tissues.

As normal conversion of linoleic acid to GLA is impaired in diabetic complications, treatment with GLA and/or with its further metabolites DGLA and AA is beneficial. Prostacyclin levels have been shown to be reduced in the nerves in diabetic animals and to be restored by treatment with GLA.

Another approach is based on damage that results from over-production of the glucose metabolite, sorbitol, in the cells of the body. Glucose can be converted to sorbitol by the enzyme aldose reductase, but this step is very slow at normal concentrations of glucose and sorbitol levels are therefore usually very low. At high concentrations of glucose, in contrast, conversion is greater and high levels of sorbitol may occur. These levels may have a variety of effects on cells, causing disturbance to the osmolarity and disrupting various aspects of cellular metabolism, including the inositol cycle. These effects have been suggested to be among the causes of diabetic complications. If this is the case then blocking the enzyme using inhibitors, or more broadly giving a material reducing the sorbitol levels, is likely to be valuable to treat/prevent diabetic complications. Such inhibitors, aldose reductase inhibitors, have been developed by many different pharmaceutical companies.

Further, a recent report (Cunningham et al, J. Am. Coll. Nutrition 13 (No. 4) 344–350 (1994)) shows ascorbic acid to be as potent as any of the aldose reductase inhibitor drugs in inhibiting the enzyme.

In studying treatments, we have developed a model of diabetic complications using the slowing of nerve conduction which takes place in the rat made diabetic by the injection of streptozotocin, which damages the insulin secreting cells of the pancreas. This slow nerve conduction can be normalised by insulin treatment. It can also be normalised by treatment with gamma-linolenic acid in various forms or by treatment with a range of aldose reductase inhibitors.

We have constructed dose response curves showing the restoration of normal nerve conduction by both GLA and the enzyme inhibitors, the experimental details being described in a variety of publications such as N. E. Cameron, M. A. Corter and S. Robertson in "Diabetes", Vol.40, pp.532–39 (1991). Essentially rats are made diabetic with streptozotocin and maintained for 6 weeks without treatment with GLA or other fatty acid, then treated for 2 further weeks with the fatty acid, either with or without other materials under test. The effect of the agent is shown as the degree of restoration of conduction velocity as compared to the untreated diabetic group.

Present Work

We have now investigated interactions between the effects of GLA and the aldose reductase inhibitor ZD5522. In initial work, each active was given at a threshold dose which would be expected to produce an approximately 5% improvement in conduction velocity in the diabetic model. It would be expected that the two treatments given together might at best be additive, leading to an improvement of the order of 10%. Instead, in several experiments, depending on the precise doses chosen, the actual improvement was in the range of 40–80%, approximately 1.5–6 times greater than would be anticipated. This is a totally unexpected effect and is of very great therapeutic significance, promising greatly increased efficacy of treatment and at the same time a lower risk of side effects because of the ability to get therapeutic effects with lower drug doses than currently used. Similar results were obtained using a second aldose reductase inhibitor, WAY 121509.

Furthermore, when ascorbate is used instead of drugs such as aldose reductase inhibitors (ARIs), there is the major advantage of use solely of natural materials, well known to be tolerated in large doses, and which moreover can very readily be used in single-compound form as ascorbyl-GLA etc.

THE INVENTION

Figure 1:
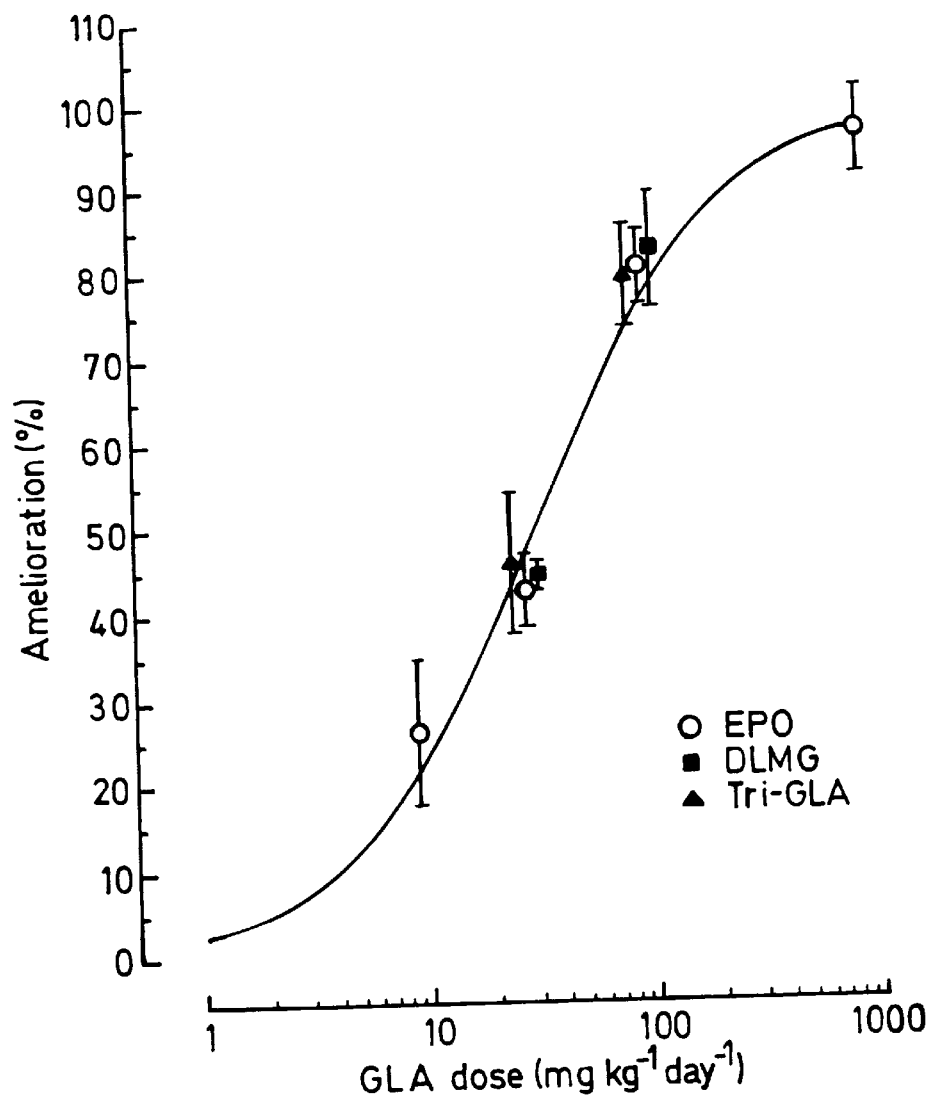
FIG. 1 is a dose-response curve for GLA in various forms, including evening primrose oil (EPO), dilinoleoyl-monogammalinolenoyl-glycerol (DLMG) and tri-gammalinolenoyl-glycerol (tri-GLA). The curve shows the percentage restoration of nerve conduction velocity towards normal in streptozotocin-diabetic rats. The curve shows the effects of the various sources of GLA when given at the same mg/kg/day doses in terms of GLA. This demonstrates that the various different forms of GLA have very similar effects.
Figure 2:
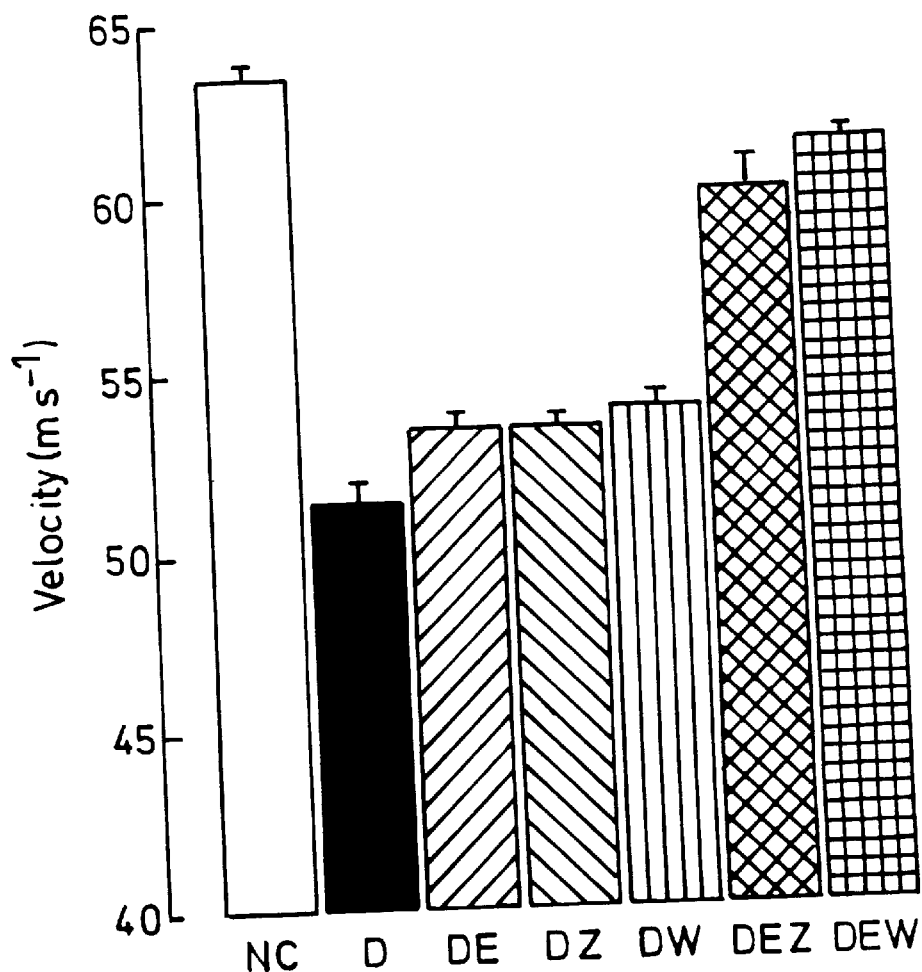
FIG. 2 shows the effects of 8 mg/kg/day GLA, 0.25 mg/kg/day ZD5522 and 0.2 mg/kg/day WAY 121509 given alone and together on nerve conduction velocity in normal and diabetic animals. ZD5522 is 3',5'-dimethyl-4'-nitromethyl-sulphonyl-2-(2-tolyl)acetanilide. WAY 121509 is spiro(isoquinoline-4(1H), 3'-pyrrolidine)-1,2',3',5'-(2H)-tetrone. The doses of the three compounds when given alone produced a small improvement in nerve conduction but the effects of either ZD5522 or WAY 121509 given together with GLA were much more than could be expected from simple additive effects of the compounds.
Figure 3:
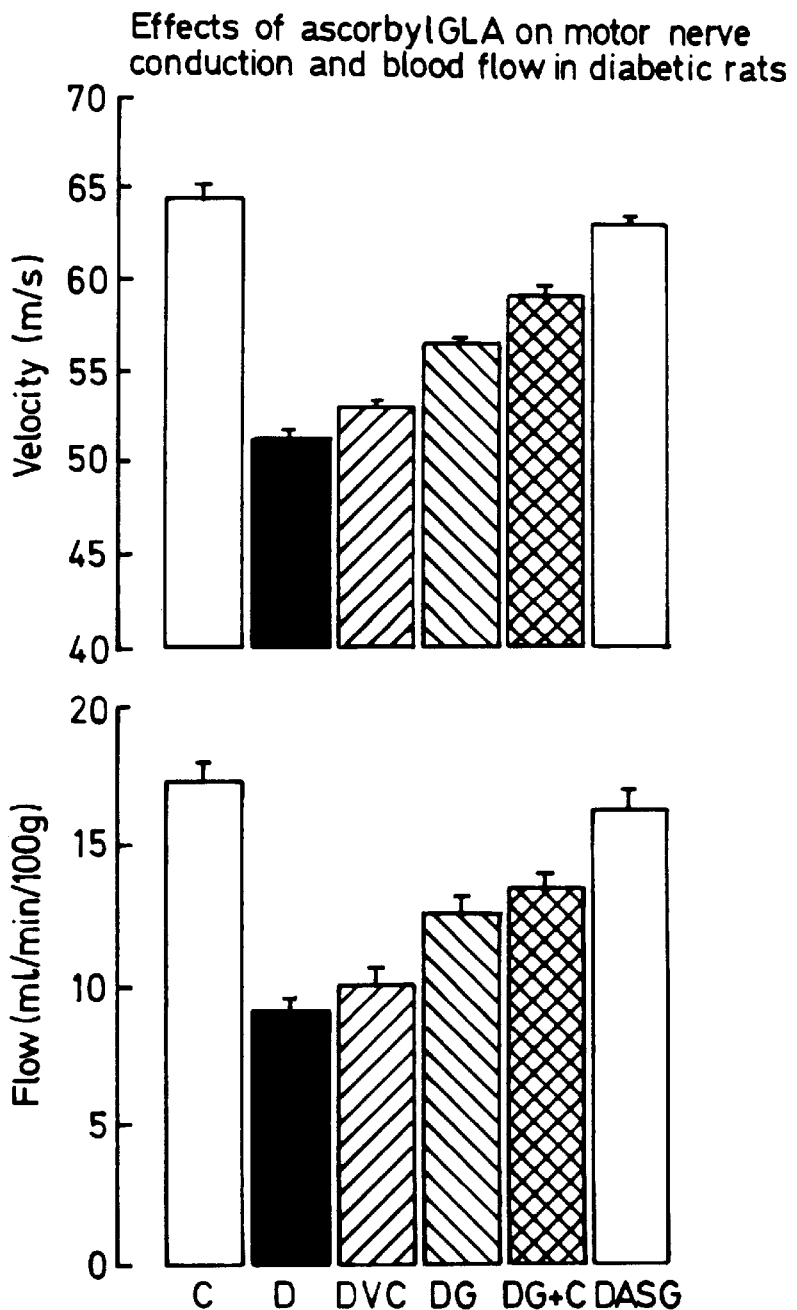
FIG. 3 shows the effects of GLA and ascorbic acid given alone and together and also the effects of the single compound ascorbyl-GLA on sciatic nerve blood flow and conduction velocity. In this case the effects of the two compounds given together were little more than additive, though that in itself is of value. However, the effect of ascorbyl-GLA given as a single compound has actions which are clearly superior to the sum of the effects of either GLA or ascorbic acid given separately and also to the effects of GLA and ascorbic acid given together. The provision of the single compound, ascorbyl-GLA, is clearly better, possibly because it delivers both components of the molecule to the required site at the same time.

In one aspect the invention thus provides a pharmaceutically acceptable composition of a 6-desaturated n-6 fatty acid, especially GLA, DGLA or AA, together with a material reducing intracellular levels of sorbitol in the body, particularly an aldose reductase inhibitor. The preferred inhibitor is ascorbate as such or in combined form as salts, esters or other derivatives, and especially when as an ester with the fatty acid, but the 'drug' ARIs may also be used.

In another aspect the invention lies in the use in treatment (including prophylactic treatment) of the long-term complications of diabetes mellitus, of a 6-desaturated n-6 fatty acid, especially GLA, DGLA or AA, together with a pharmaceutically acceptable material reducing intracellular levels of sorbitol in the body, particularly when said material is an aldose reductase inhibitor. Ascorbate, as above, is preferred. Normally the active materials will be given together, but the invention covers administration of the fatty acid and material reducing sorbitol levels separately but so as to bring about their simultaneous presence in the effective amounts in the body.

In a further aspect, the invention concerns the preparation of medicaments for treatment (including prophylactic treatment) of the long-term complications of diabetes, using the active materials together or using one of them the medicament in that case being for a treatment in which the other is also being administered but separately.

Still further the invention provides as novel compounds ascorbate esters of 6-desaturated n-6 fatty acids (other than GLA or DGLA), particularly ascorbyl-AA, and the same when for use in any therapy.

The invention thus particularly lies in the treatment of complications of diabetes, especially but not limited to neuropathy, retinopathy, nephropathy and cardiovascular disease, by the combined administration of an EFA preferably chosen from GLA, DGLA or AA, together with ascorbate or other material able to inhibit the enzyme aldose reductase or more generally reduce bodily sorbitol levels. The actives may be provided in separate formulations to be administered together (or if separately then at least for effective amounts to be present in the body at the same time), or in a combined dosage form, and in either case in any appropriate presentation. Especially, ascorbyl-GLA, ascorbyl-DGLA or ascorbyl-AA may be used. Presentation may be as capsules, tablets, powders, microcapsules, emulsions, liposomes, micelles or any other appropriate form of oral, enteral, parenteral or topical presentations, all as well known to those skilled in the art.

The dose of the EFA may be for example in the range from 10 mg to 10 g per day, preferably 100 mg to 5 g per day and very preferably 300 mg to 2 g per day and dosage unit forms may contain such amounts or submultiples thereof. The dose of aldose reductase inhibitor will be appropriate to the material chosen and can only be noted here as in terms of effective daily amounts within a broad range covering all known such drugs but without implications that the extremes of the range namely 0.01 to 100 mg/kg/day apply to each drug, and noting also that any material with the ability to reduce the conversion of glucose to sorbitol may be used. Examples are ponalrestat, tolrestat and epalrestat, all at 0.1 to 20 mg/kg/day or, as with the broad range, corresponding amounts calculated as for a 70 kg adult. In the case of ascorbate the dose may for example be 10 mg to 5 g per day, preferably 50 mg to 2 g, calculated as ascorbic acid when as ascorbyl-GLA or other combined form.

The EFA may be in any pharmaceutically acceptable form which leads to the availability of the EFA within the body. Particularly suitable forms, besides ascorbyl-EFAs, include mono-, di- and triglycerides, free fatty acids, cholesterol esters, salts, amides and phospholipids of various types, but no pharmaceutically acceptable form is excluded. Natural evening primrose oil, or evening primrose oil enhanced in its content of DLMG (di-linoleoyl-mono-gammalinolenoyl-glycerol) is particularly convenient, or DLMG from any source. Fatty alcohols derived from EFAs may also be used.

The following examples illustrate the invention and are in terms of compositions of EFAs and known aldose reductase inhibitor drugs, then compositions of EFAs and ascorbate, and finally, preparation of EFA esters of ascorbate. The 'drug' ARIs also, where of suitable chemical structure, may be as compounds with the EFAs, and such single compounds are likely to be preferable to the two agents given separately.

EXAMPLES

Aldose Reductase Inhibitor Drugs Compositions

There are many different aldose reductase inhibitors (ARIs) and many others are likely to be discovered. Equally, drugs may be found which inhibit sorbitol production by different mechanisms. The following are some specific examples of formulations using known ARIs:

1. 400 mg hard or soft gelatin capsules containing GLA, DGLA or AA in triglyceride, free fatty acid, salt or other form to be coadministered with the ARI ponalrestat provided in 300 mg tablets, 2 capsules of the EFA and 1 tablet of the ponalrestat to be taken each morning and evening.

2. As example 1 except that the ARI is tolrestat, 200 mg tablets bd (twice daily).

3. As example 1 except that the ARI is epalrestat, 150 mg tablets bd or 100 mg tds (three times daily).

4. As example 1 except that instead of the above ARIs, ADN-138 (Ono), SNK-860 (Sanwa), M16209 (Fuji), ZD5522 (Zeneca) or WAY 121509 (Wyeth) is used.

5. As examples 1 to 4 except that the EFA and the ARI are combined together within the same dosage form whether that be a capsule, tablet, metered container or any other appropriate form known to those skilled in the art such as microcapsules, powders, liposomes, reverse liposomes or forms for enteral, oral, parenteral or other routes of administration.

6. As examples 1 to 4 except that the EFA is formulated as 200 mg, 300 mg, 500 mg, 600 mg, 800 mg or 1 g capsules and is given in a total dose of from 200 mg to 3 g per day.

EXAMPLES

Ascorbate Compositions

7. GLA, DGLA or AA as in example 1 or 6 is administered with 50 mg to 2 g ascorbic acid daily in tablet or other suitable formulation.

8. Ascorbyl-GLA, for example synthesised as below, or Ascorbyl-DGLA or Ascorbyl-AA correspondingly, is used to give daily ascorbic acid amounts as last, in particular in any of particular in any of the following forms:

(a) Tablets containing 50, 100, 250, 500 or 750 mg of Ascorbyl GLA, Ascorbyl DGLA or Ascorbyl AA either as such or with an appropriate excipient.

(b) Soft gelatin or hard gelatin capsules containing 50, 100, 250 or 500 mg Ascorbyl GLA, Ascorbyl DGLA or Ascorbyl AA dissolved in free fatty acids enriched in GLA or DGLA or in triglycerides in which one or more of the moieties are selected from GLA or DGLA.

(c) Emulsion, powders, liquids, slurries, or solutions for oral, enteral or parenteral administration of ascorbyl-GLA or ascorbyl-DGLA. For example emulsions may be prepared with appropriate emulsifying agents such as egg phospholipids or oat galactolipids to give a final emulsion in which ascorbyl-GLA, ascorbyl-DGLA or ascorbyl-AA makes up 2%–30% by weight of the emulsion.

(d) Ointments, creams, lotions, shampoos, or other appropriate formulations for the topical application of ascorbyl-GLA, ascorbyl-DGLA or ascorbyl-AA.

EXAMPLES

Synthesis of Ascorbyl-EFAs

9. Ascorbyl-GLA.

In the synthesis hydrogen chloride gas (2.0 g) is bubbled into N,N-dimethyl acetamide (26.5 ml) at 0° C. To the resultant slurry was added a slurry of ascorbic acid (9.69 g) in dichloromethane (13.25 ml) and the mixture is stirred at 0° C. until solution occurs. To this solution at 0° C. under nitrogen, is added, z,z,z-octadeca-6,9,12-trienoyl chloride (GLA acid chloride) (14.8 g) over a period of 4 hours and the resulting mixture is allowed to stand at the above temperature for 18 hours and room temperature for 1 hour. On cooling to 0° C., ethyl acetate (200 ml) and water (100 ml) is added and the mixture stirred for 1 hour. The organic layer is washed with brine (5×100 ml), dried ($Na_2SO_4$) and evaporated at 50° C./10 mmHg then 50° C./0.1 mm/4 hours to give ascorbic acid-6-[(z,z,z)-octedeca-6,9,12-trienoate] (yield as conducted 18.25 g, 88%) as a pale yellow wax.

10. Ascorbyl-GLA.

Dry hydrogen chloride gas (5.4 parts,g.) is passed into a mixture of anhydrous dimethyl acetamide (71.25 parts, ml) and dry dichloromethane (40 parts, ml) at (−2) −2° C. with stirring. To this mixture is added ascorbic acid (26.05 parts, g.) and the mixture is stirred until a clear solution is obtained. Over a period of 4–5 hr at (−2)–2° C., z,z,z-octadeca-6,9,12-trienoyl chloride (γ-linolenoyl chloride) (39.6 parts,g.) is added dropwise under nitrogen and after stirring for a further 1–2 hr, the mixture is allowed to stand at (−2)–2° C. for 20–24 hrs. The dichloromethane is then removed in vacuo (25–30° C./20–30 mb) and to the resultant sludge is added water (250 parts, ml) with stirring. Saturated brine (250 parts, ml) is added and the mixture is stirred vigorously for 10–15 min under nitrogen. After standing for 10–15 min, the product separates as a semi solid, top layer. The aqueous layer is removed and the above treatment with water and brine is repeated 4 more times. The product is then dissolved in ethyl acetate (250 parts, ml), extracted with water (2×50 parts, ml) and dried (anhydrous sodium sulphate). The ethyl acetate is removed in vacuo (35–40° C./20–30 mb) and the residue dissolved in ethanol (250 parts, ml). The ethanol is removed in vacuo (35–40° C./20–30 mb then 70–75° C./0.1–0.5 mb/5 hr) to give ascorbic acid-6-(z,z,z-octadeca-6,9,12-trienoate), ascorbyl-GLA, as a pale yellow wax.

11. Ascorbyl-DGLA

By proceeding in a similar manner but replacing the γ-linolenoyl chloride with an equivalent amount of z,z,z-eicosa-8,11 14-trienoyl chloride, (dihomo-γ-linolenoyl chloride) there is prepared ascorbic acid-6-(z,z,z-eicosa-8,11,14-trienoate), ascorbyl-DGLA, as a pale yellow wax.

12. Ascorbyl-AA

By proceeding in a similar manner but replacing the γ-linolenoyl chloride with an equivalent amount of z,z,z,z-eicosa-5,8,11,14-tetraenoyl chloride, (arachidonyl chloride) there is prepared ascorbic acid-6-(z,z,z,z-eicosa-5,8,11,14-tetraenoate), ascorbyl-AA, as a pale yellow wax.

We claim:

1. A pharmaceutical composition comprising a 6-desaturated n-6 fatty acid together with a material reducing intracellular levels of sorbitol in the body, said material being a material other than ascorbic acid or ascorbate in any form, wherein the combination when administered to treat long term complications of diabetes mellitus provides a synergistic reduction of intracellular levels of sorbitol in the body.

2. The composition according to claim 1, wherein said 6-desaturated n-6 fatty acid is selected from the group consisting of gammalinolenic acid (GLA), dihomogamma-linolenic acid (DGLA) or arachidonic acid (AA).

3. The composition according to claim 1 wherein said material is an aldose reductase inhibitor.

4. A method of treating long term complications of diabetes mellitus comprising administering to a patient in need thereof an effective amount of a 6-desaturated n-6 fatty acid together with a pharmaceutically acceptable material reducing intracellular levels of sorbitol in the body, with the proviso that if said material is ascorbate then the ascorbate is present in combined form with said 6-desaturated n-6 fatty acid as an ascorbyl-essential fatty acid (EFA) ester, wherein in said treatment the combination provides a synergistic reduction of intracellular levels of sorbitol in the body.

5. The method according to claim 4 wherein said 6-desaturated n-6 fatty acid is selected from the group consisting of gammalinolenic acid (GLA), dihomogamma-linolenic acid (DGLA) or arachidonic acid (AA).

6. The method according to claim 4 wherein said material is an aldose reductase inhibitor.

7. The method according to claim 4 wherein said material is ascorbate present in combined form with said 6-desaturated n-6 fatty acid as an ascorbyl-EFA ester.

8. The method according to claim 4, wherein an ascorbyl-EFA is administered.

9. The method according to claim 4 wherein ascorbyl-GLA, ascorbyl-DGLA or ascorbyl-AA is administered.

10. The method according to claim 4, wherein the fatty acid and material reducing sorbitol levels are administered separately but so as to bring about their simultaneous presence in the effective amounts in the body.

11. The method according to claim 4, wherein said treatment is prophylactic treatment.

* * * * *